US012680090B1

(12) United States Patent
Wilson et al.

(10) Patent No.: US 12,680,090 B1
(45) Date of Patent: \*Jul. 14, 2026

(54) PHARMACEUTICAL FORMULATIONS, METHODS FOR TREATING CHEMICAL WARFARE AGENT EXPOSURE, AND MODIFIED BIOMOLECULES

(71) Applicant: TELEDYNE FLIR DEFENSE, INC., North Billerica, MA (US)

(72) Inventors: David Wilson, Pittsburgh, PA (US); Jennifer L. Poole, Delmont, PA (US); Jeremy P. Walker, Oakmont, PA (US)

(73) Assignee: TELEDYNE FLIR DEFENSE, INC., North Billerica, MA (US)

( * ) Notice: Subject to any disclaimer, the term of this patent is extended or adjusted under 35 U.S.C. 154(b) by 84 days.

This patent is subject to a terminal disclaimer.

(21) Appl. No.: 18/520,769

(22) Filed: Nov. 28, 2023

Related U.S. Application Data

(60) Continuation of application No. 17/320,192, filed on May 13, 2021, now Pat. No. 11,866,743, which is a division of application No. 15/994,621, filed on May 31, 2018, now abandoned.

(60) Provisional application No. 62/513,330, filed on May 31, 2017.

(51) Int. Cl.
*C12N 9/16* (2006.01)
*A61K 38/46* (2006.01)

(52) U.S. Cl.
CPC ........ *C12N 9/16* (2013.01); *C12Y 301/08001* (2013.01); *A61K 38/465* (2013.01)

(58) Field of Classification Search
CPC ..................................................... C12N 9/16
See application file for complete search history.

(56) References Cited

U.S. PATENT DOCUMENTS

| | | | |
|---|---|---|---|
| 6,541,230 | B1 | 4/2003 | Gordon et al. |
| 10,260,054 | B2 | 4/2019 | Pegan et al. |
| 10,301,608 | B2 | 5/2019 | Faushel et al. |
| 10,363,290 | B2 | 7/2019 | Perlroth et al. |
| 2015/0376594 | A1 | 12/2015 | Walker et al. |
| 2016/0009757 | A1 | 1/2016 | Lihme |
| 2016/0184445 | A1 | 6/2016 | Periroth et al. |
| 2016/0355792 | A1 | 12/2016 | Pegan et al. |

FOREIGN PATENT DOCUMENTS

| | | |
|---|---|---|
| WO | 2000/064539 | 11/2000 |
| WO | 2001/036665 | 5/2001 |
| WO | 2015/196106 | 12/2015 |

OTHER PUBLICATIONS

Zhang et al., "Nanoscavenger Provides Long-Term Prophylactic Protection Against Nerve Agents in Rodents", Science Translational Medicine Research Article and Supplemental Materials, Jan. 2, 2019, United States, 25 pages.

Andreopoulos et al., "Photoimmobilization of Organophosphorus Hydrolase within a PEG-Based Hydrogel", Biotechnology and Bioengineering vol. 65, 1999, Germany, pp. 579-588.

(Continued)

*Primary Examiner* — Yong D Pak
(74) *Attorney, Agent, or Firm* — K&L Gates LLP

(57) ABSTRACT

Pharmaceutical formulations that can include at least one genetically modified OPH enzyme are provided. Methods for treating chemical warfare agent exposure are also provided. Modified biomolecules are also provided.

10 Claims, 7 Drawing Sheets

Enzyme Activity Retention

1. OPH(YT) native
2. OPH(YT) with initiator
3. OPH(YT) PEGMA conjugate, 54 KDa average
4. OPH(YT) PEGMA conjugate, 130 KDa average
5. OPH(YT) PEGMA conjugate, 175 KDa average

(56)          References Cited

OTHER PUBLICATIONS

Ashani et al. "Estimation of the Upper limit of Human Butyrylcholinesterase Dose Required for Protection Against Organophosphates Toxicity: A Mathematically Based Toxicokinetic Model", Toxicological Sciences vol. 77. 2004, United Kingdom, pp. 368-367.

Ashani et al., "In Vitro Detoxification of Cyclosarin in Human Blood Pre-Incubated Ex Vivo with Recombinant Serum Paraoxonases", Toxicology Letters, vol. 206, Sep. 2011, Netherlands, pp. 24-28.

Bigley et al., "Enzymatic Neutralization of the Chemical Warfare Agent VX: Evolution of Phosphotriesterase for Phosphorothiolate Hydrolysis", Journal of the American Chemical Society vol. 135, 2013, United States, pp. 10426-10432.

Cherny et al., "Engineering V-Type Nerve Agents Detoxifying Enzymes Using Computationally Focused libraries", ACS Chemical Biology vol. 8, 2013, United States, pp. 2394-2403.

Fishburn, The Pharmacology of PEGylation: Balancing PD with PK to Generate Novel Therapeutics, Journal of Pharmaceutical Sciences vol. 97, No. 10, Oct. 2008, United States, pp. 4167-4183.

Goldsmith et al., "Catalytic Efficiencies of Directly Evolved Phosphotriesterase Variants with Structurally Different Organophosphorus Compounds in Vitro", Archives of Toxicology vol. 90, 2016, Germany., pp. 2711-2724.

Hurst, "Medical Management of Chemical Casualties Handbook", 5th Edition, U.S. Army Medical Research Institute of Chemical Defense, 2014, United States. 190 pages.

Lenz et al. , "Butyrylcholinesterase as a Therapeutic Drug for Protection Against Percutaneous VX", Chemico-Biological Interactions vol. 187, 2010, Netherlands, pp. 249-252.

Lillie et al., "Potential Military Chemical/biological Agents and Compounds", Army, Marine Corps, Navy, Air Force, Jan. 2005, United States, 318 pages.

Mumford et al, "Post-Exposure Therapy with Recombinant Human BuChE Following Percutaneous VX Challenge in Guinea-Pigs", NIH Public Access Author Manuscript, published in Toxicology Letters vol. 206. Sep. 25, 2011, Netherlands, pp. 29-34.

Novikov et al., "Improved Pharmacokinetics and Immunogenicity Profile of Organophosphorous Hydrolase by Chemical Modification with Polyethylene Glycol", Journal of Controlled Release vol. 146, 2010, Netherlands, pp. 318-325.

Pisal et al,, "Delivery of Therapeutic Proteins", NIH Public Access Author Manuscript, Published in Journal of Pharmaceutical Sciences vol. 99, Jun. 2010, United States, pp. 2557-2575.

Tsai et al., "Enzymes for the Homeland Defense• Optimizing Phosphotriesterase for the Hydrolysis of Organophosphate Nerve Agents", Biochemistry vol. 51, 2012, United States, pp. 6463-6475.

Wilson et al., "High-Throughout Functionalization of Organophosphate Scavenger Enzymes for Improved Pharmacokinetics and Warfighter Protection", Flir Systems. Inc., 2016, United States, 1 page.

Studer, "Residue mutations and their impact on protein structure and function: detecting beneficial and pathogenic changes", Biochem. J (2013), 449, 581-594.

Nanocs, 2013.

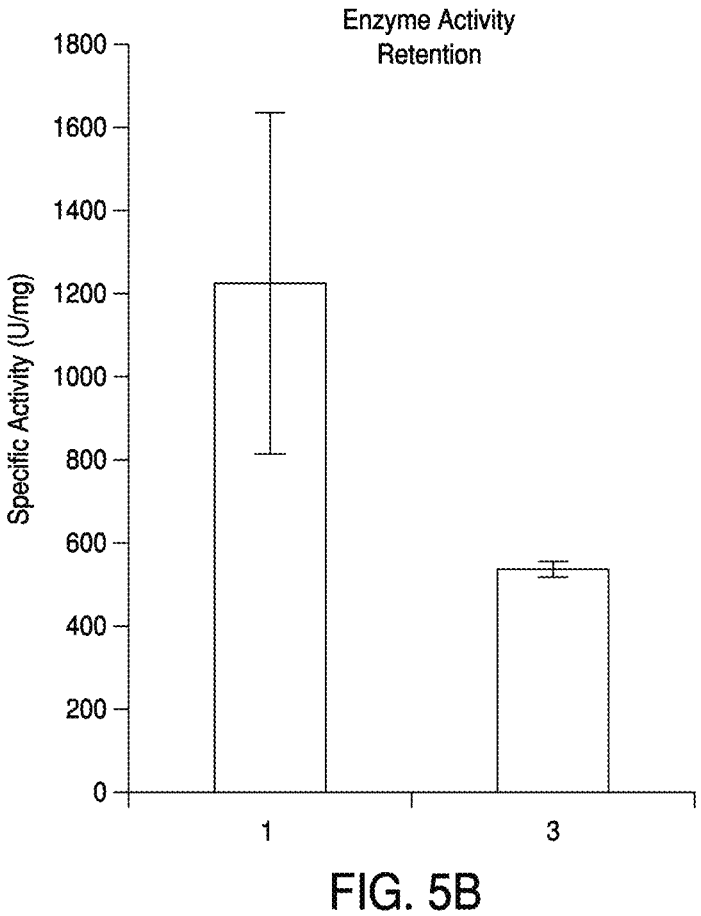
FIG. 5B
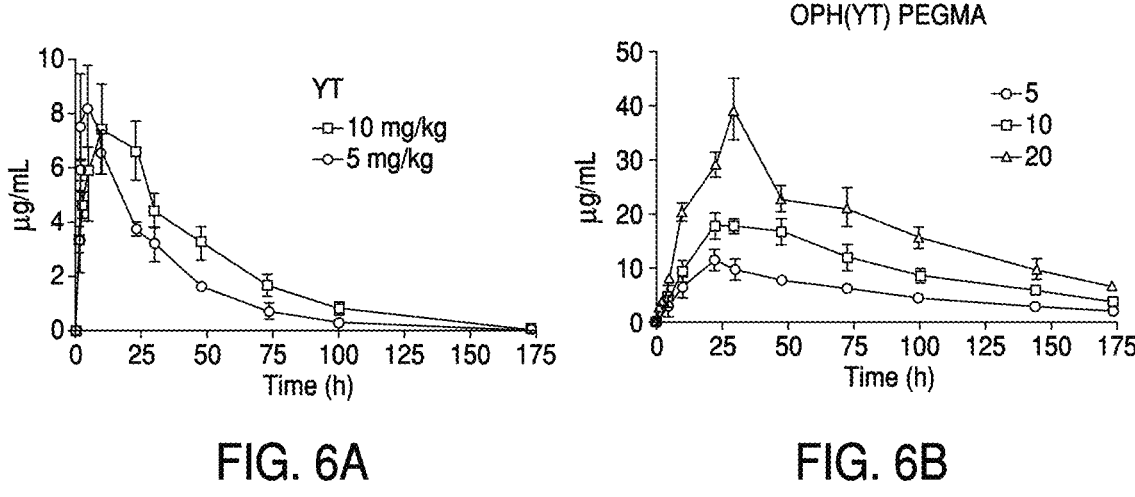
FIG. 6A                    FIG. 6B

PHARMACEUTICAL FORMULATIONS, METHODS FOR TREATING CHEMICAL WARFARE AGENT EXPOSURE, AND MODIFIED BIOMOLECULES

CROSS REFERENCE TO RELATED APPLICATION

The present application claims priority under 35 U.S.C § 120 as a continuation application of co-pending U.S. application Ser. No. 17/320,192, filed on May 13, 2021, which is a divisional of U.S. application Ser. No. 15/994,621, filed May 31, 2018, which claims priority to and benefit of U.S. Provisional Application No. 62/513,330 filed on May 31, 2017. Each of the forgoing applications is hereby incorporated by reference in its entirety into the present application.

TECHNICAL FIELD

The present disclosure provides pharmaceutical formulations, methods for treating chemical warfare agent exposure, and modified biomolecules. Compositions and/or methods are provided that can be utilized to treat those exposed to chemical warfare agents, or to prophylactically treat those that may be exposed to chemical warfare agents.

BACKGROUND

Exposure to nerve agents can result in rapid, devastating, and often lethal, biological effects. Nerve agents are highly toxic and easily adsorbed into the body through multiple routes of entry (eyes, respiratory tract, skin). Once in circulation, nerve agents covalently modify endogenous cholinesterase enzymes, causing paralysis, asphyxiation, and often death. Current therapies for nerve agent exposure involve the use of nucleophilic chemical reactivators of endogenous enzyme (oximes).

The use of enzymatic scavengers, such as human butylcholinesterase (HuBChE), have been developed as potential therapeutics for nerve agent exposure. However, limitations exist for the HuBChE therapy approach. In the case of the human derived BChE, pharmacokinetics can vary widely based on the enzyme's tertiary structure as well as any post-translational modification (dimer vs. tetramer, glycosylated vs. non-glycosylated respectively). Control of the composition becomes a critical component for the dosing and pharmacokinetics/pharmacodynamics of the therapeutic. In addition, native BChE is a stoichiometric scavenger, and thus a large dose is typically necessary that is at least equivalent to the agent challenge to provide protection. Furthermore, unmodified proteins tend to be cleared rapidly from circulation, so the dose must be even higher to ensure a sufficient scavenger loading to enable full agent detoxification prior to protein clearance.

Modification of the BuChE to improve the PK/PD and enable use over extended timeframes or as a prophylaxis is limited since BChE is a stoichiometric scavenger, this further increases the molecular weight of the therapeutic and thus markedly increases the size of the required dose. At present no one such catalyst embodies a rate sufficient to address all nerve agents; however a cocktail of protein catalysts, modified with the optimal PK/PD modifiers, could provide the profile needed to generate a useful therapeutic for all nerve agents.

The present disclosure provides pharmaceutical formulations, methods for treating chemical warfare agent exposure, and modified biomolecules. The formulations, methods, and/or biomolecules can be considered in some embodiments to include a catalytic enzyme as a formulation component for the treatment of nerve agent poisoning as a prophylaxis or post-exposure therapeutic.

SUMMARY OF THE DISCLOSURE

The present disclosure provides pharmaceutical formulations that can include at least one genetically modified OPH enzyme.

The present disclosure also provides methods for treating chemical warfare agent exposure. The methods can include administering to a subject a pharmaceutically effective amount of a pharmaceutical formulation comprising a genetically modified OPH enzyme.

The present disclosure also provides modified biomolecules. These biomolecules can include a genetically modified OPH enzyme having at least one polymer chain extending therefrom. The present disclosure provides pharmaceutical formulations and/or methods for treating chemical warfare agent exposure. In accordance with example implementations, the formulations, methods, and/or biomolecules can be used to treat those with potential for being exposed to chemical warfare agents, i.e., prophylactically, or those already exposed to chemical warfare agents.

DRAWINGS

Embodiments of the disclosure are described below with reference to the following accompanying drawings.

FIG. 5B is a representation of data indicating activity of the modified biomolecules of FIG. 5A, FIGS. 6A, 6B; 6C, and 6D are representations of data associated with biomolecules of the present disclosure.

Figure 7A:
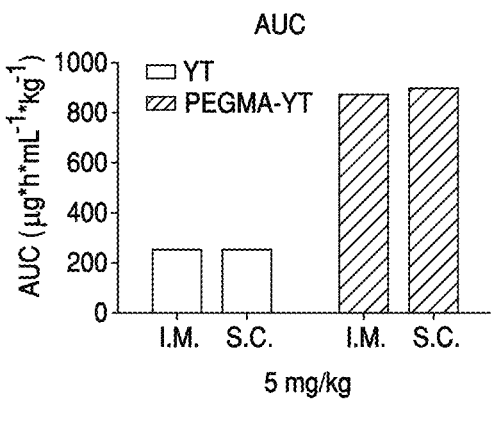
Figure 7B:
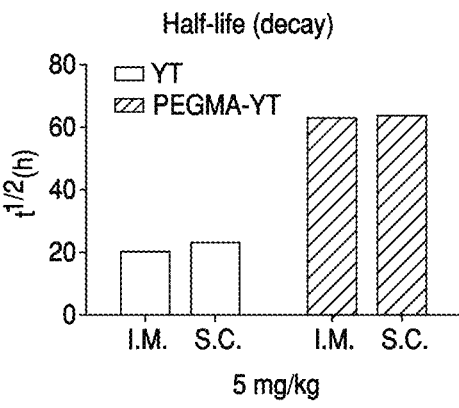
Figure 7C:
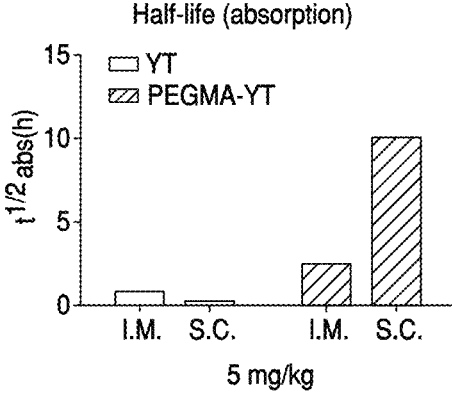

FIGS. 7A, 7B, and 7C are representations of data associated with biomolecules according to the present disclosure.

Figure 8:
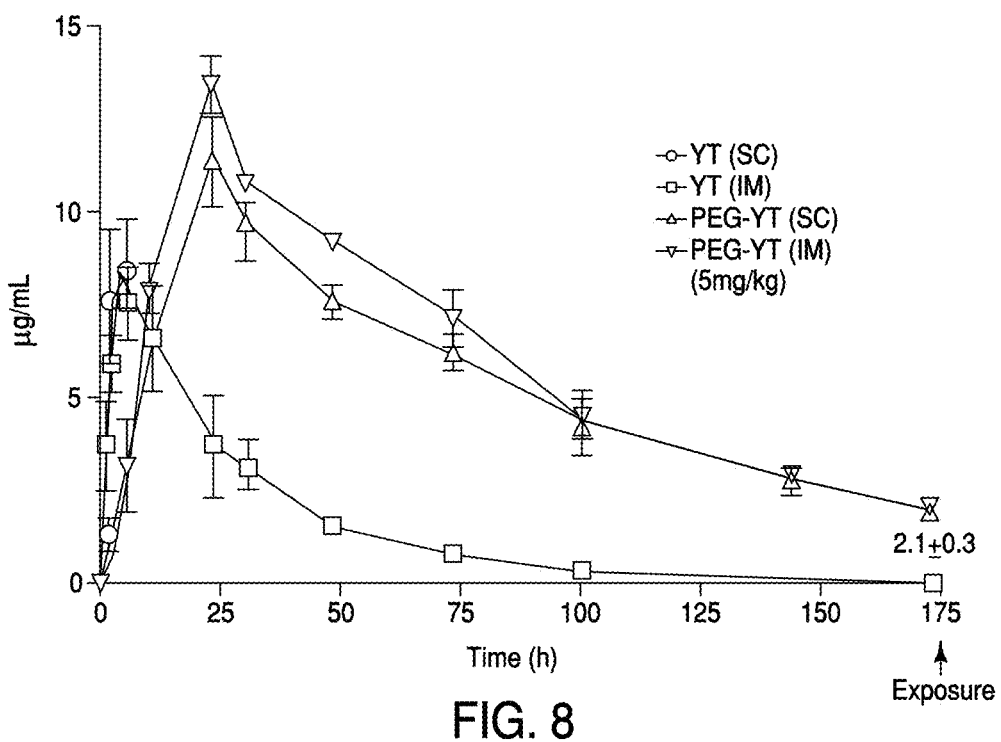
Figure 9:
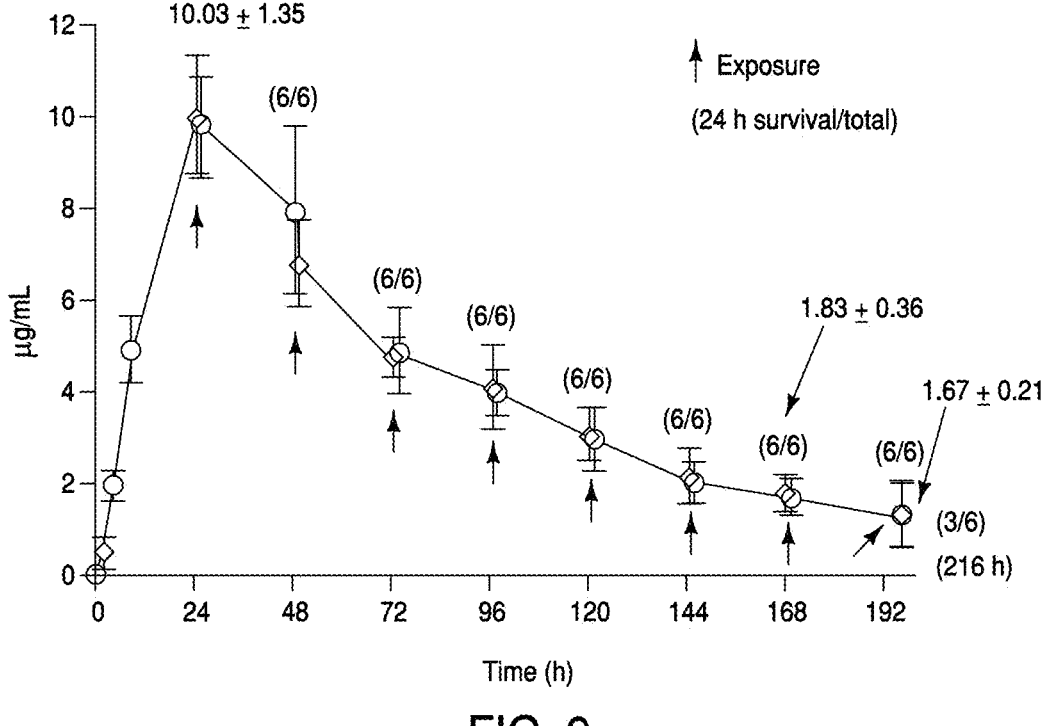

FIG. 8 is a representation of data associated with biomolecules according to the present disclosure, FIG. 9 is a representation of data associated with biomolecules of the present disclosure.

Figure 10:
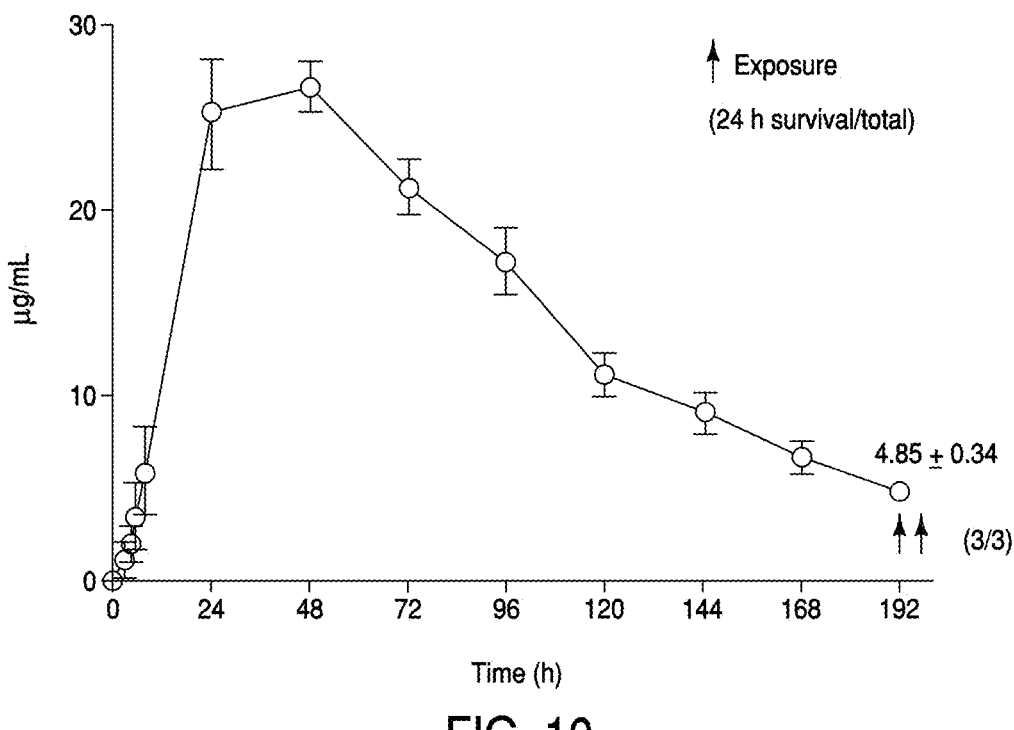

FIG. 10 is a representation of data associated with biomolecules of the present disclosure.

Figure 11:
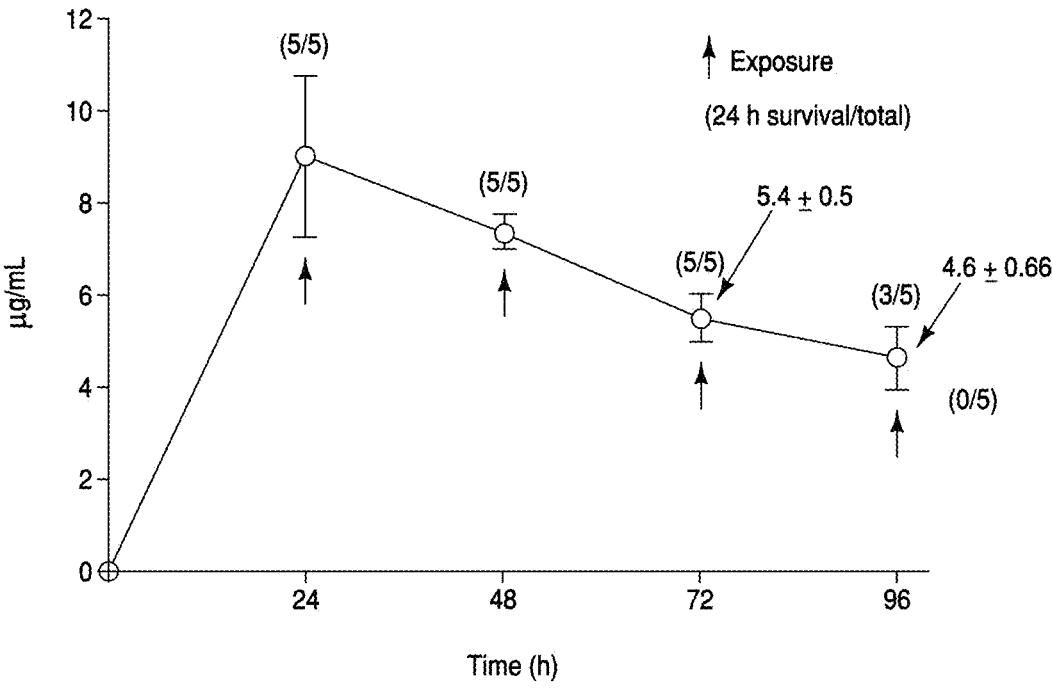

FIG. 11 is a representation of data associated with biomolecules of the present disclosure.

Figure 12:
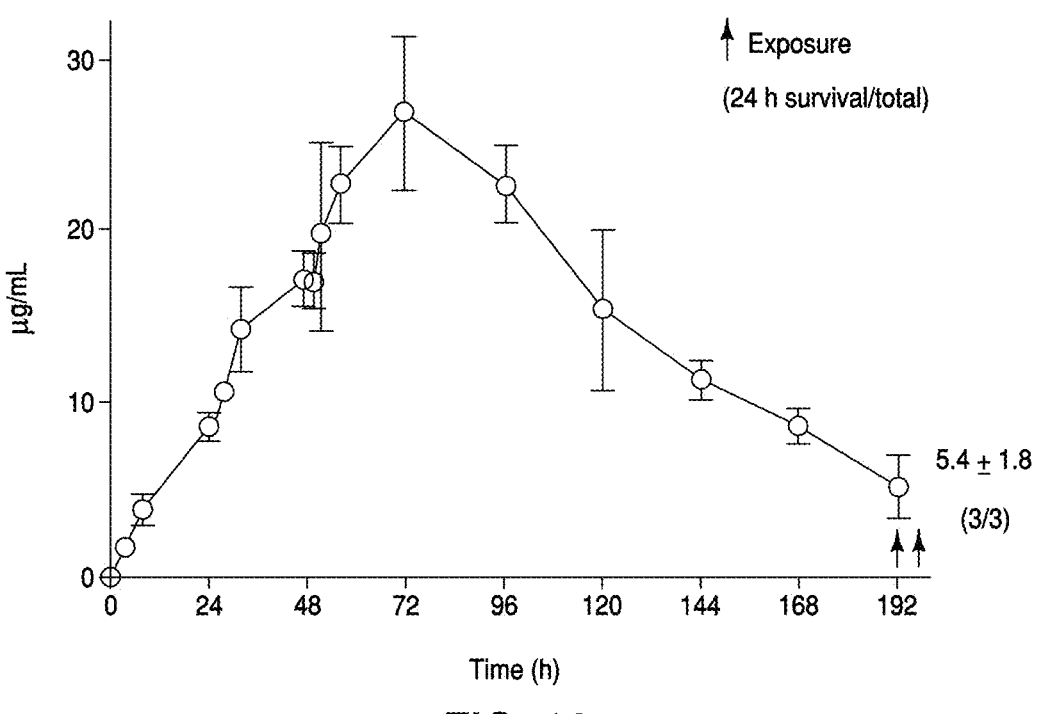

FIG. 12 is a representation of data associated with biomolecules of the present disclosure.

Figure 13:
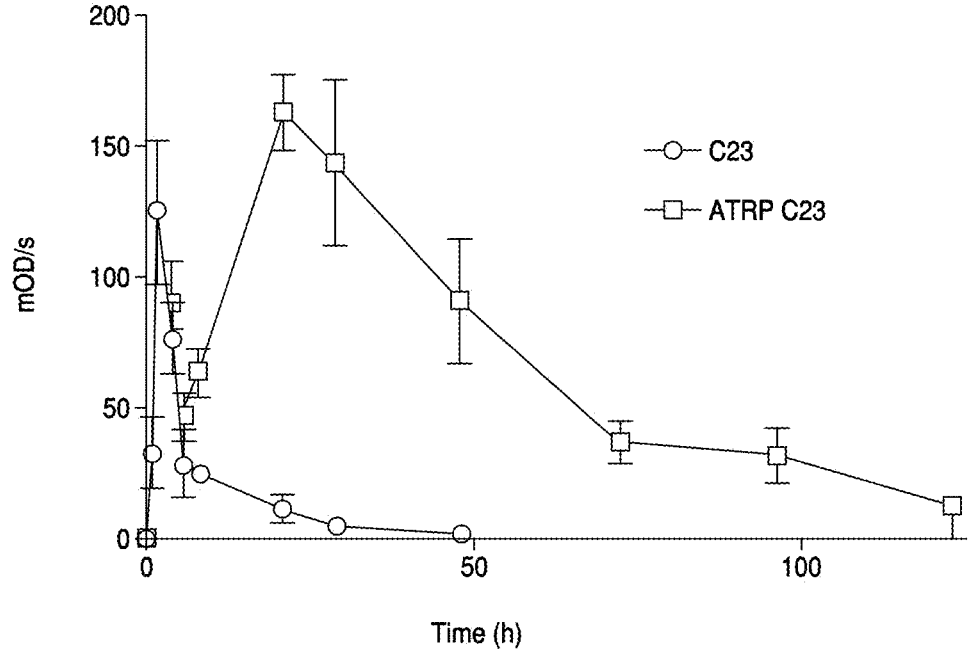

FIG. 13 is a representation of data associated with biomolecules of the present disclosure.

DESCRIPTION

This disclosure is submitted in furtherance of the constitutional purposes of the U.S. Patent Laws "to promote the progress of science and useful arts" (Article 1, Section 8).

Figure 1:
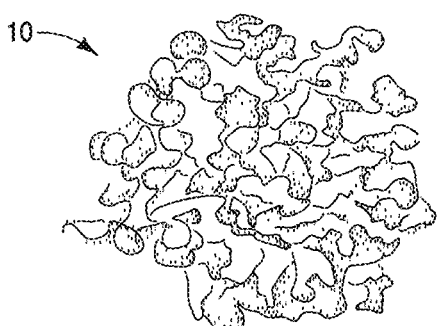
FIG. 1 is a representation of a genetically modified OPH enzyme that can be utilized as a biomolecule within the pharmaceutical formulations, and/or methods of the present disclosure.

The present disclosure will be described with reference to FIGS. 1-13. Referring first to FIG. 1, a modified biomolecule 10 is shown and provided. Biomolecule 10 can be a genetically modified OPH enzyme. Example genetically modified OPH enzymes can include the YT modification, the C23 modification, or the IVH3 modification. Additional modifications are contemplated. Such as those modifications that would include a genetic sequence that leads to improved catalytic activity up to the diffusion limit of nerve agent hydrolysis; these modifications would also be included. In accordance with example implementations, the in vivo catalytic activity of these modified biomolecules, when exposed to G-series chemical warfare agents can be greater than $1\times10^7$ $k_{cat}/k_m$, and/or when exposed to V-series chemical warfare agents, the catalytic activity can be greater than $1\times10^5$ $k_{cat}/k_m$.

In accordance with example implementations using specific plasmids (YT, C23, or IVH3), an amino acid sequence of the enzyme to be genetically modified is reverse translated to the nucleic acid sequence. The DNA sequence is then optimized for expression in *E. coli* by removing rare codons and optimizing for codon adaptability, mRNA structure, and for various cis-elements in transcription and translation. The gene can be synthesized de novo, purified and then cloned into the pET20b+ expression vector. Last, via DNA sequencing, the gene can be verified to be in the correct orientation and that no mutations have occurred.

To begin the expression phase, the chosen plasmid is transformed into chemically competent BL21(DE3)pLyss *E. coli* cells and selected for positively transformed colonies on antibiotic plates. Starter cultures can be prepared overnight at 37° C. in Luria Broth (LB), which is used to seed a ≥5 L culture in Terrific Broth (TB). The cultures can be fermented at 37° C. until the log phase of growth, the temperature can be reduced to 25° C. and Isopropyl b-D-1-thiogalactopyranoside (IPTG) added to induce the enzyme expression. The cultures can be maintained at 25° C., two more doses of IPTG added, the cultures allowed to ferment overnight, and then harvested via centrifugation after 24 hours. The recovered cell pellets can be frozen at −80° C., thawed, and resuspended in 50 mM HEPES, 100 µM $CoCl_2$.

The bacteria may then be lysed while stirring on ice with two rounds of sonication and centrifuge to remove the insoluble proteins and cell membranes. The supernatant can be subjected to a protamine sulfate treatment and another round of centrifugation to remove gross contaminating nucleic acids. Then, the modified OPH can be precipitated with 60% ammonium sulfate, the supernatant discarded, and the enzyme resuspended in 50 mM HEPES, 100 µM $CoCl_2$. The modified OPH can be filtered and injected onto a fast protein liquid chromatography (FPLC) instrument equipped with a Superdex 200 pg size exclusion column (SEC). The modified OPH-containing fractions can be collected, pooled, and then passed over a DEAE anion exchange column; the modified OPH binds to the column, and can be eluted with an 80 mM sodium chloride wash. Via ultrafiltration, the pure enzyme can be provided in a 50 mM Sodium Borate buffer, sterilized and stored at +4° C. until use in a pharmaceutical formulation and/or until polymer addition.

Figure 2:
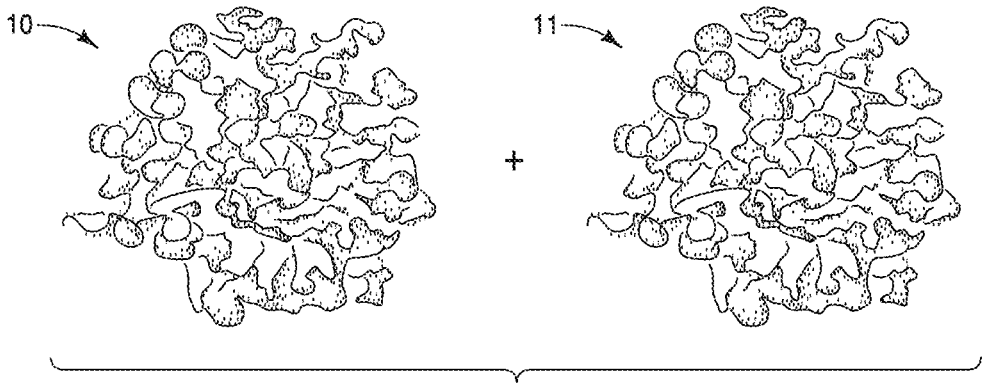
FIG. 2 is a pair of genetically modified OPH enzymes that may be utilized as biomolecules in the pharmaceutical formulations and/or methods of the present disclosure.

Referring next to FIG. 2, a pair of genetically modified OPH enzymes can be provided as part of the pharmaceutical formulation as well. In accordance with example implementations, one of the OPH enzymes can be a YT modification, and the other can be an IVH3 or C23 modification.

Figure 3:
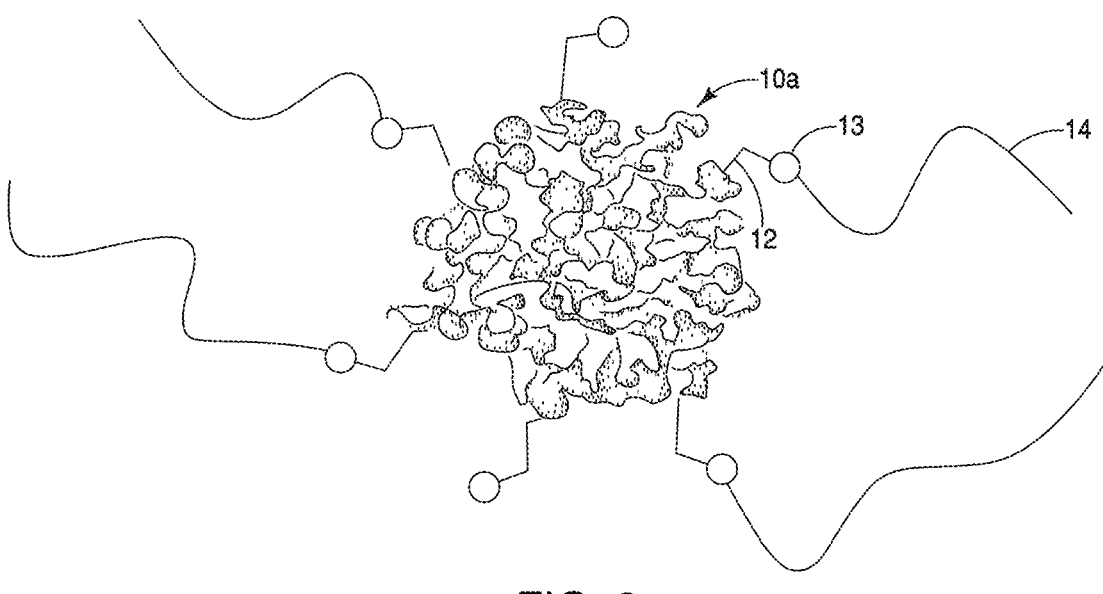
FIG. 3 is another genetically modified OPH enzyme that includes at least one polymeric structure extending therefrom that may be utilized as a modified biomolecule in the pharmaceutical formulations and/or methods of the present disclosure.

Referring next to FIG. 3, a biomolecule 10a can be a chemically modified genetically modified OPH enzyme. Biomolecule 10a can include at least one polymeric chain. This chain can be coupled to biomolecule 10 via the modification of the biomolecule with an active site 12 and coupling point 13. Polymer chain 14 can include PEG or PEGMA, for example. Nondegradable PEG alternatives can include poly(N-vinylpyrrolidone), polyglycerol, poly(N-(2-hydroxypropyl) methacrylamide), polyoxazolines. Degradable PEG alternatives can include poly[oligo(ethyleneglycol)methyl methacrylate], and copolymers containing. Degradable non-PEG alternatives can include poly(sulfobetaine methacrylate), poly(carboxybetaine methacrylate), and carbonate or phosphoryl choline-based polymers. Naturally degradable PEG alternatives can include polysaccharides, poly(amino-acid) materials and recombinant peptides, and nanoparticulate or colloidal systems (liposomes, polymeric microspheres or nanoparticles).

Biomolecules 10a can be prepared by modifying biomolecules 10, for example. The genetically modified OPH can be chemically modified with a small molecule initiator, N-hydroxysuccinimide-tetra-ethylene-glycol bromide (NHS-TEG-Br), for example. The initiator can be added at a 15:1 initiator to lysine ratio in a final 16% v/v dimethyl sulfoxide (DMSO) solution and the reaction allowed to progress for 1 hour and then the excess removed via filtration. A fluoraldehyde free amine assay can be used to determine the absolute number of initiators attached to the surface of the biomolecule. The buffer can be exchanged with 15 mM Tris-HCl, pH 7.6 and the OPH concentrated to above 2.5 mg/mL. The initiated protein (1.6 mg/mL final concentration) can then be mixed with polyethylene-glycol methyl-ether methacrylate (PEGMA) (1.6% v/v final concentration) in 15 mM Tris-HCl, pH 7.6 and the reaction deoxygenated with argon bubbled for 30 minutes. The components can be placed into another vessel containing a mixture of copper (I) chloride (2.1 mM final concentration), bipyridyl (1.8 mM final concentration), and cobalt (II) chloride (0.46 mM final concentration) also in 15 mM Tris-HC, pH 7.6, that had been deoxygenated it for about 30 minutes. The reaction can progress in this vessel for 3 hours and prior to quenching with oxygen. The small molecule reaction components can then be removed via filtration, and the enzyme-polymer conjugate exchanged to a 50 mM HEPES buffer, pH 8.0, and concentrated to greater than 5 mg/mL. Removal of all reagents can be verified via UV spectrophotometry and the full exchange to the 50 mM HEPES by conductivity measurements and the conjugate sterile filtered and then stored at +4° C. until use.

These biomolecules can be part of a pharmaceutical formulation that includes Human Serum Albumin (HSA), lipoprotein, glycoprotein, globulins, and/or IGg, for example. In accordance with example implementations, the pharmaceutical formulation or the methods of the present disclosure can include providing a genetically modified OPH enzyme that includes a polymer chain in combination with genetically modified OPH enzymes that do not include polymer chains. The formulations and the methods can also include providing both different genetically modified OPH enzymes that both include polymer chains, for example.

Figure 4:
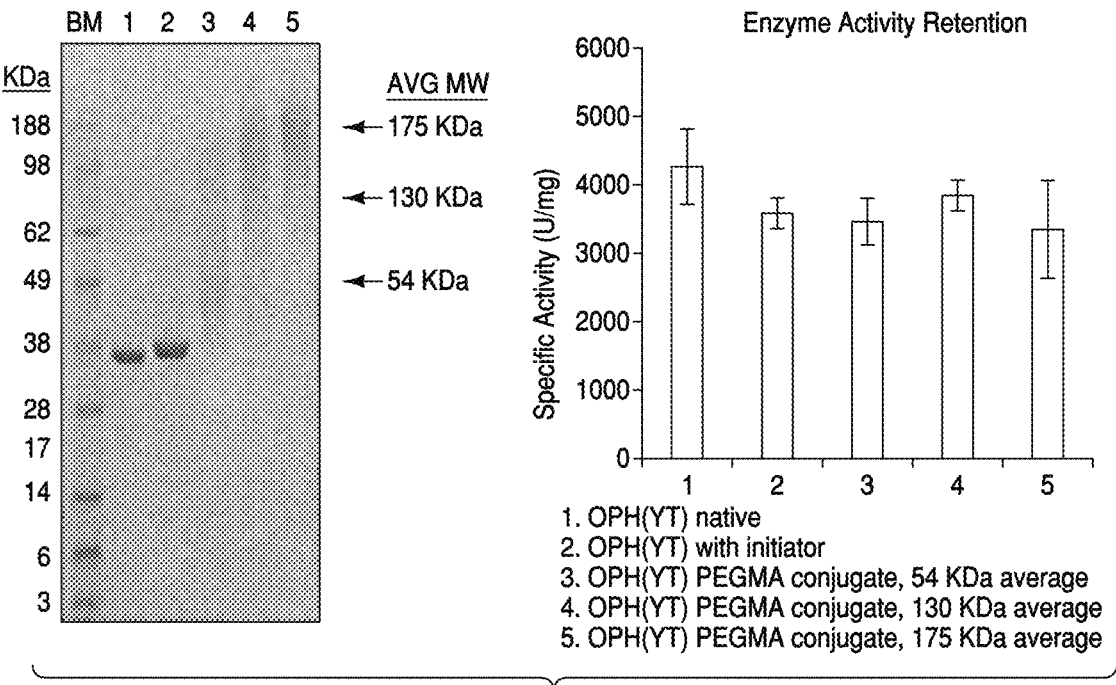
FIG. 4 is a representation of data indicating activity and size of the modified biomolecules of the present disclosure.

Referring next to FIG. 4, in accordance with example implementations, a genetically modified OPH enzyme such as the OPH(YT) enzyme can have polymers attached thereto via controlled radical polymerization. Example polymers that can be attached include PEGMA, and these polymer chains can be added in different lengths. In accordance with example implementations, native YT modified OPH enzyme as well as YT enzymes including polymer chains can be injected into guinea pigs at 5 mg/kg and blood taken from the animals at various timepoints. Catalyst activity can be determined by residual blood activity against paraoxon at each timepoint. The overall trends can demonstrate activity extended consistent with the length of the conjugate. As can be seen in FIG. 4, the first column is the OPH(YT) native, the second column is the OPH(YT) with initiator, the third column is the OPH(YT) PEGMA conjugate with a 54 KDa average, the fourth column is the OPH(YT) PEGMA conjugate with 130 KDa average, and the fifth column is the OPH(YT) PEGMA conjugate with 175 KDa average.

Figure 5A:
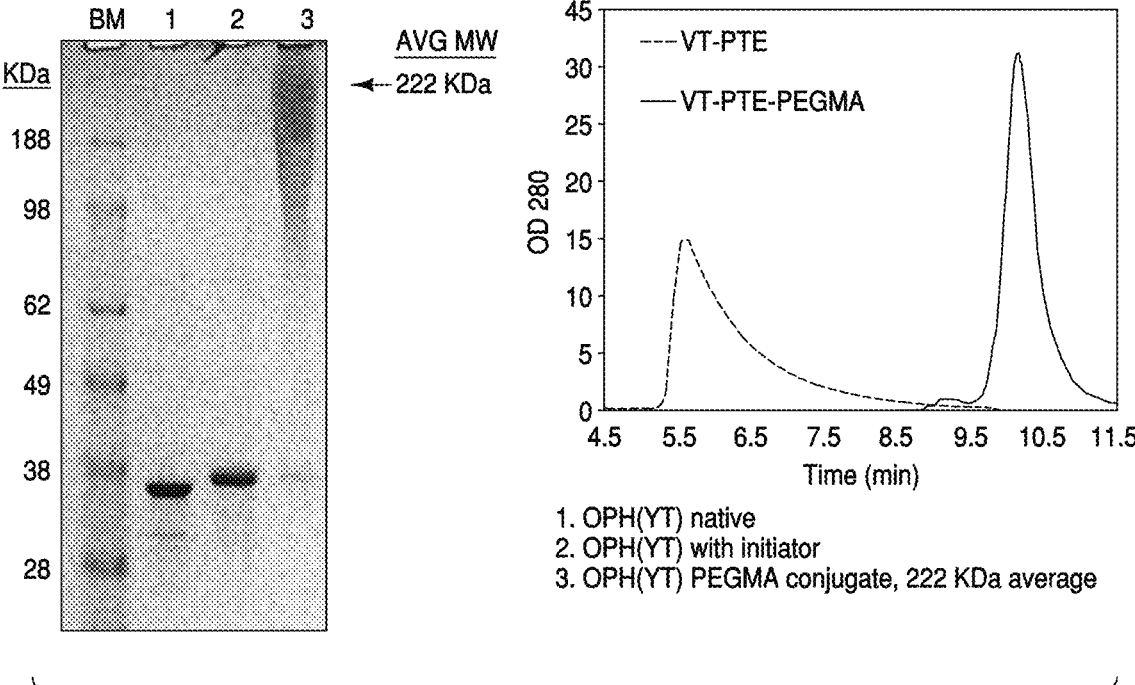
FIG. 5A is a representation of data indicating size of the modified biomolecules of the present disclosure.
Figure 6C:
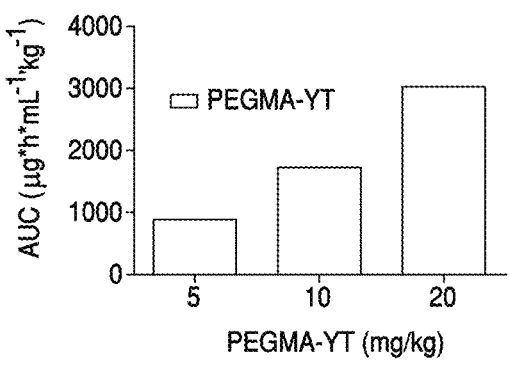
Figure 6D:
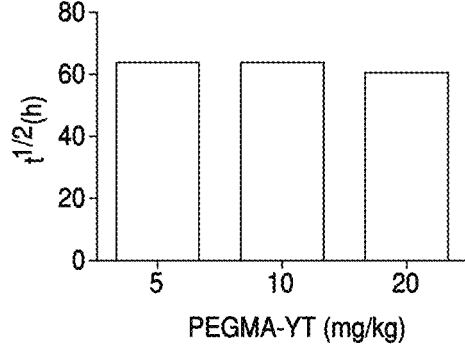

Referring next to FIG. 5A, biomolecules can be provided in larger scales, for example, the OPH(YT) conjugate including the polymers can have a size commensurate with the polymer added thereto. In accordance with FIG. 5A, the first OPH(YT) can be native, the second OPH(YT) can be with an initiator, and the third OPH(YT) can be a PEGMA conjugate at 222 KDa average. In accordance with FIG. 5B as shown, the enzyme activity of the first OPH(YT) native can be compared with the enzyme activity of the third, and a 600 specific activity can be determined, demonstrating that the enzyme modification while impacting the activity still provides activity that is greater than the required therapeutic threshold of $1\times10^7$ $k_{cat}/k_m$.

Referring next to FIGS. 6A, 6B, 6C, and 6D, a series of data is depicted graphically. This data is commensurate with the data represented in Table 1 and Table 2 below. As can be seen, OPH(YT) PEGMA showed dose dependent bioavailability (AUC ↑ with ↑ dose). Also, the OPH(YT) PEGMA showed greater enzyme load as compared to OPH(YT), and OPH(YT) PEGMA showed longer half-life of clearance as compared to OPH(YT), and OPH(YT) PEGMA showed greater protective efficacy as compared to OPH(YT).

TABLE 1

| Dose (mg · kg$^{-1}$) | PEG | $R^2$ k | Points | k (h$^{-1}$) | $C_0$ (µg · mL$^{-1}$) | t½ (h) | $R^2$ $k_a$ | Points | $k_a$ (h$^{-1}$) | t½$_{abs}$ (h) | AUC (µg · h · mL$^{-1}$ · kg$^{-1}$) | Avg Injection Vol (mL) |
|---|---|---|---|---|---|---|---|---|---|---|---|---|
| 5.0 (s.c.) | No | 0.932 | 7 | 0.029 | 7.0 | 23.9 | 1.0000 | 2 | 2.195 | 0.3 | 261.2 | 0.392 |
| 10.0 (s.c.) | No | 0.968 | 6 | 0.023 | 9.6 | 29.2 | 0.9836 | 3 | 0.3735 | 1.9 | 383.0 | 0.755 |
| 5.0 (s.c.) | Yes | 0.922 | 6 | 0.010 | 12.8 | 64.0 | 0.9932 | 4 | 0.06804 | 10.2 | 904.6 | 0.391 |
| 10.0 (s.c.) | Yes | 0.930 | 6 | 0.010 | 26.1 | 64.0 | 0.9852 | 4 | 0.04691 | 14.8 | 1,760 | 0.803 |
| 20.0 (s.c.) | Yes | 0.950 | 4 | 0.011 | 48.2 | 61.6 | 0.9931 | 6 | 0.08173 | 8.5 | 3,073 | 1.57 |

TABLE 2

| Guinea Pigs (n) | Enzyme | Injection Route | Concentration | 24 hours Survival post GB Exposure 2 × LD$_{50}$ Day 7.2 (173 h) | Bioavailability µg/ml @ 173 h |
|---|---|---|---|---|---|
| 3 | YT | SC | 5 mg/kg | 0/3 | 0.08 ± 0.05 |
| 3 | YT | SC | 10 mg/kg | 2/3 | 0.18 ± 0.06 |
| 3 | YT-PEGMA | SC | 5 mg/kg | 3/3 | 2.0 ± 0.35 |
| 3 | YT-PEGMA | SC | 10 mg/kg | 3/3 | 3.8 ± 1.04 |
| 2 | YT-PEGMA | SC | 20 mg/kg | 3/3 | 6.8 ± 0.11 |

Referring next to FIGS. 7A-C and FIG. 8, in the context of the data represented in Table 3 and Table 4 below, injection of OPH(YT) and OPH(YT) PEGMA can be provided subcutaneously and intramuscularly. As can be seen from the data, OPH(YT) PEGMA showed greater enzyme load as compared to OPH(YT) for both routes, and regardless of administration route, OPH(YT) PEGMA showed greater protective efficacy as compared to OPH(YT), and the subcutaneous and intramuscular generated similar enzyme load to the subject.

TABLE 3

| Dose (mg · kg⁻¹) | PEG | $R^2$ k | Number of points | k (h⁻¹) | $C_0$ (µg · mL⁻¹) | $t^{1/2}$ (h) | $R^2$ $k_a$ | Number of points | $k_a$ (h⁻¹) | $t^{1/2}_{abs}$ (h) | $T_{max}$ (h) | AUC (µg · h · mL⁻¹ · kg⁻¹) |
|---|---|---|---|---|---|---|---|---|---|---|---|---|
| 5.0 (s.c.) | No | 0.9323 | 7 | 0.029 | 7.0 | 23.9 | 1.0000 | 2 | 2.195 | 0.3 | | 261.2 |
| 5.0 (s.c.) | Yes | 0.9225 | 6 | 0.010 | 12.8 | 64.0 | 0.9932 | 4 | 0.06804 | 10.2 | | 904.6 |
| 5.0 (i.m.) | No | 0.9744 | 1 | 0.032 | 8.3 | 21.3 | 0.9944 | 3 | 0.7395 | 0.9 | | 255.9 |
| 5.0 (i.m.) | Yes | 0.8750 | 6 | 0.010 | 11.7 | 63.2 | 0.9659 | 4 | 0.2595 | 2.7 | | 876.2 |
| 10.0 (s.c.) | No | 0.9681 | 6 | 0.023 | 9.6 | 29.2 | 0.9836 | 3 | 0.3735 | 1.9 | | 383.0 |
| 10.0 (s.c.) | Yes | 0.9305 | 6 | 0.010 | 26.1 | 64.0 | 0.9852 | 4 | 0.04691 | 14.8 | | 1,760 |
| 20.0 (s.c.) | Yes | 0.9502 | 4 | 0.011 | 48.2 | 61.6 | 0.9931 | 6 | 0.08173 | 8.5 | | 3,073 |

TABLE 4

| Guinea Pigs (n) | Enzyme | Injection Route | Dose (mg/kg) | Exposure GB@ 173 h (SC route) | 24 hours Survival post | Bioavailability µg/ml @ 173 h |
|---|---|---|---|---|---|---|
| 3 | YT | Subcutaneous | 5 | $2 \times LD_{50}$ | 0/3 | 0.077 ± 0.05 |
| 3 | YT-PEGMA | Subcutaneous | 5 | $2 \times LD_{50}$ | 3/3 | 2.0 ± 0.35 |
| 3 | YT | Intramuscular | 5 | $2 \times LD_{50}$ | 0/3 | 0.02 ± 0.01 |
| 3 | YT-PEGMA | Intramuscular | 5 | $2 \times LD_{50}$ | 3/3 | 2.13 ± 0.35 |

Referring next to Table 5 below, as was previously demonstrated, protection against $2 \times LD_{50}$ of GB in guinea pigs with subcutaneous administration of a single bolus of OPH(YT) PEGMA can be achieved. At these GB challenge levels, full animal survival can be observed. The GB challenge dose can then be increased to determine the level of protection afforded by a 5 mg/kg dose of OPH(YT) PEGMA. As Table 5 demonstrates below, there has been 100% animal survival (6/6) at 24 hours post single $5 \times LD_{50}$ GB dose, and 50% survival observed (2/4) at 24 hours post single $10 \times LD_{50}$ GB dose.

TABLE 5

| Guinea Pigs (n) | Enzyme | Injection Route | Dose (mg/kg) | Exposure @Tmax $x LD_{50}$ GB (SC route) | 24 hours Survival post | PEGMA-YT (mg/kg) @ exposure Avg ± stdev |
|---|---|---|---|---|---|---|
| 6 | PEGMA-YT | SC | 5 | 2 | 6/6 | 10.03 ± 1.35 |
| 6 | PEGMA-YT | SC | 5 | 5 | 6/6 | 9.0 ± 1.8 (5 animals) |
| 4 | PEGMA-YT | SC | 5 | 10 | 2/4 | 6.8 ± 0.8 (3 animals) |

In accordance with example implementations, methods are provided for treating chemical warfare agent exposure, and the methods can include administering to a subject a pharmaceutically effective amount of a pharmaceutical formulation comprising a genetically modified OPH enzyme. The subject can be mammalian. Human subjects can be war fighters and the subjects may be administered the formulations prophylactically. In accordance with example implementations, because of the load and the exposure, it is clear that the administration can be performed prophylactically, thereby providing a war fighter, for example, with a bolus of a pharmaceutical formulation and providing at least some protection against warfare chemical agent exposure. In accordance with example implementations, the pharmaceutically effective amount in the subject can be provided for greater than or equal to 10 days after the administering, and/or at least greater than or equal to 5 days after the administering. In accordance with example implementations, the pharmaceutically effective amount can include providing 1, 5, 10, and/or 20 mg of modified biomolecule for every kg of subject. In accordance with example implementations, these modified OPH enzymes which are the part of pharmaceutical formulation can include at least one polymer chain, and that polymer chain can include PEGMA as described herein, and there may be more than one active biomolecule of different kinds, so the formulation can include different OPH enzymes, and these OPH enzymes may or may not include at least one polymer chain as described herein.

Referring next to FIG. 9, data associated with Table 6 below is provided. In accordance with example implementation, it has been shown that a 5 mg/kg dose of OPH(YT) PEGMA may protect 100% subject survival (6/6) on days 1-8, 5 mg/kg OPH(YT) on day 0 protected against $2 \times LD_{50}$ for up to 8 days, and on the 9th day, 50% survival (3/6) can be observed.

TABLE 6

| Dose (mg · kg⁻¹) | PEG | $R^2 k$ | Number of points | $k$ (h⁻¹) | $C_0$ (µg · mL⁻¹) | $t^{1/2}$ (h) | $R^2 k_a$ | Number of points | $k_a$ (h⁻¹) | $t^{1/2}_{abs}$ (h) | AUC (µg · h · mL⁻¹ · kg⁻¹) |
|---|---|---|---|---|---|---|---|---|---|---|---|
| 5.0 (n = 6) | Yes | 0.889 | | 0.01111 | 11.8 | 62.4 | 0.9712 | | 0.08778 | 7.9 | 849.8 |
| 5.0 (SC from slide 2 n = 3) | Yes | 0.922 | 6 | 0.010 | 12.8 | 64.0 | 0.9932 | 4 | 0.06804 | 10.2 | 904.6 |

The data of Table 6 and FIG. 9 can be compiled from assays of mammals. For example, Guinea Pigs: 6 animals Dose: 5 mg/kg Admin Route: S.C. Injection: Single bolus @ Time=0 h; Capillary Whole Blood Collected @:Pre-admin, 1, 5, 10, 24, 25, 48, 49, 72, 73, 96, 97, 120, 121, 144, 145, 168, 169, 192 h; (double blood draws were taken immediately prior to exposure and one hour after: one blood sample will be used to measure RBC AChE Activity the other for plasma/PD assessment); Protective Efficacy Exposure: $2\times LD_{50}$ GB via S.C. injection (opposite flank) in 24 h intervals (first exposure @ $T_{max}=24$ h); Survival assessed every 24 h post-exposure (24 h survival/total); Exposure @ 192 h (8 days)=cumulative dose=$16\times LD_{50}$.

Referring next to FIG. 10, data associated with protective efficacy against GB is provided, demonstrating periodic dosing. In accordance with example implementations, 100% subject survival has been shown after 24 hours. The data of FIG. 10 can be from a study of pharmacodynamics of PEGMA-YT: Sequential Dosing 3× (24 h apart) w/exposure to $7\times LD_{50}$ of GB every at 192 h (8 days) Guinea Pigs: 3 animals Dose: 5 mg/kg Admin Route: S.C.; Injection. Sequential Single bolus @ Time=0, 24, 48 h; Capillary Whole Blood Collected @:Pre-admin, 1, 4, 8, 24, 25, 28, 32, 48, 49, 52, 56, 72, 96, 120, 144, 168, 192 h. Protective Efficacy; Exposure: $2\times LD_{50}+5\times LD_{50}$ of GB via S.C. injection (opposite flank); $1^{st}$ exposure ($2\times LD_{50}$) @ 192 h followed by $2^{nd}$ exposure ($5\times LD_{50}$) @ 196 h–cumulative $7\times LD_{50}$; Survival assessed every 24 h post-exposure (24 h survival/total); No signs/symptoms after $1^{st}$ exposure; mild to moderate signs after $2^{nd}$ exposure; 3/3 24 h post-exposure.

Referring next to FIG. 11, additional data shows efficacy during periodic exposure of subjects to subjects treated with the pharmaceutical formulations of the disclosure. As can be seen, 100% animal survival is provided on days 1-3, and at 5 mg/kg OPH(YT) on day 0 protected against $5\times LD_{50}$ for up to 3 days. On the $4^{th}$ day, 60% survival (3/5) can be observed, and n the $5^{th}$ day, no subjects survived. The data of FIG. 11 can be from a study of Pharmacodynamics of PEGMA-YT w/repeated exposure to $5\times LD_{50}$ of GB every 24 h; Guinea Pigs: 5 animals Dose: 5 mg/kg Admin Route: S.C. Injection: Single bolus @ Time=0 h; Capillary Whole Blood Collected @: Pre-admin, 24, 48, 72, 96 h; Protective Efficacy; Exposure: $5\times LD_{50}$ GB via S.C. injection (opposite flank) in 24 h intervals (exposure @ 24, 48, 72, 96 h); Survival assessed every 24 h post-exposure (24 h survival/total).

Referring next to FIG. 12, data showing the protective efficacy against GB is provided, with 100% animal survival after 24 hours when dosing 5 mg/kg OPH(YT) PEGMA (3×, 24 hr apart), and assessing the protection assessed against GB challenge at day 8 with a $7\times LD_{50}$ of GB total ($2\times LD_{50}+5\times LD_{50}$). The data of FIG. 12 can be from a study of Pharmacodynamics of PEGMA-YT: Sequential Dosing 3× (24 h apart) w/exposure to $7\times LD_{50}$ of GB every at 192 h (8 days; Guinea Pigs: 3 animals Dose: 5 mg/kg; Admin Route: S.C.; Injection: Sequential Single bolus @ Time=0, 24, 48 h;

Capillary Whole Blood Collected @: Pre-admin, 1, 4, 8, 24, 25, 28, 32, 48, 49, 52, 56, 72, 96, 120, 144, 168, 192 h. Protective Efficacy; Exposure: $2\times LD_{50}+5\times LD_{50}$ of GB via S.C. injection (opposite flank); $1^{st}$ exposure ($2\times LD_{50}$) @ 192 h followed by $2^{nd}$ exposure ($5\times LD_{50}$) @ 196 h–cumulative $7\times LD_{50}$; Survival assessed every 24 h post-exposure (24 h survival/total); No signs/symptoms after $1^{st}$ exposure; mild to moderate signs after $2^{nd}$ exposure; 3/3 24 h post-exposure.

Referring next to FIG. 13, a comparison of the C23 modification of the OPH enzyme is made to the wild type OPH with a $T_{max}$ at 2 hours and the enzyme activity returning to baseline around 40 hours post-administration. A markedly different profile was measured for ATRP-C23 with a $T_{max}$ at 29 hours. The AUC was an order of magnitude greater for ATRP-C23 (C23, 777; ATRP-C23, 8285), PEGylation of C23 can substantially enhance the persistence of ATRP-C23 in circulation following subcutaneous administration.

Finally, with reference to Table 7 below, a pretreatment cocktail can be prepared with of IVH3 & YT, as well as a native enzyme that has not been PEGylated, as well as an agent challenge given 20 minutes post treatment, as well as mild nerve agent exposure symptoms in subjects exposed to VX at 60 minutes, demonstrating that all subjects were asymptomatic at 24 hours.

TABLE 7

| Treatment (PTE Cocktail) | n | Challenge (2.5 × LD50) | Symptoms | 24 Hour Survival |
|---|---|---|---|---|
| 20 mg/kg IVH3-PTE and 5 mg/kg YT-PTE | 2 | VX | Mild | 2/2 |
| 20 mg/kg IVH3-PTE and 5 mg/kg YT-PTE | 2 | VR | None | 2/2 |
| 20 mg/kg IVH3-PTE and 5 mg/kg YT-PTE | 2 | GB | None | 2/2 |
| 20 mg/kg IVH3-PTE and 5 mg/kg YT-PTE | 2 | GD | None | 2/2 |
| 20 mg/kg IVH3-PTE and 5 mg/kg YT-PTE | 2 | GF | None | 2/2 |

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents,

The invention claimed is:

1. A pharmaceutical formulation comprising a composition and a pharmaceutically-acceptable buffer, wherein the composition comprises:

a first organophosphorus hydrolase (OPH) protein:polymer conjugate that comprises:

at least a first genetically-modified OPH YT protein; and at least a first polymer produced via controlled radical polymerization from a molecular initiator, wherein the molecular initiator is conjugated to the first genetically-modified OPH YT protein and the polymer comprises polyethylene glycol methyl-ethyl methacrylate (PEGMA) chain;

wherein an in vivo $k_{cat}/k_m$ of the protein:polymer conjugate is >1×10$^7$ for at least one G-series chemical warfare agent.

2. The pharmaceutical formulation of claim 1, wherein the protein:polymer conjugate has a molecular weight in a range of 175 kDa to 222 kDa.

3. The pharmaceutical formulation of claim 1, wherein the formulation further comprises a second OPH protein:polymer conjugate, wherein the second OPH protein:polymer conjugate comprises at least a second, genetically modified OPH protein, selected from the group consisting of OPH YT protein, OPH C23 protein, and OPH IVH3 protein.

4. The pharmaceutical formulation of claim 1, wherein the molecule initiator is N-hydroxysuccinimide-tetra-ethylene-glycol bromide (NHS-TEG-Br).

5. A pharmaceutical formulation comprising a composition and a pharmaceutically-acceptable buffer, wherein the composition comprises:

a first organophosphorus hydrolase (OPH) protein:polymer conjugate that comprises:

at least a first genetically-modified OPH YT protein; and at least a first polymer conjugated thereto, the polymer comprising a polyethylene glycol methyl-ethyl methacrylate (PEGMA) chain;

wherein an in vivo $k_{cat}/k_m$ of the protein:polymer conjugate is >1×10$^7$ for at least one G-series chemical warfare agent.

6. The pharmaceutical formulation of claim 1, wherein the protein:polymer conjugate has a molecular weight in a range of 54 kDa to 130 kDa.

7. The pharmaceutical formulation of claim 1, wherein the protein:polymer conjugate has a molecular weight in a range of 130 kDa to 175 kDa.

8. The pharmaceutical formulation of claim 5, wherein the protein:polymer conjugate has a molecular weight in a range of 54 kDa to 130 kDa.

9. The pharmaceutical formulation of claim 5, wherein the protein:polymer conjugate has a molecular weight in a range of 130 kDa to 175 kDa.

10. The pharmaceutical formulation of claim 5, wherein the protein:polymer conjugate has a molecular weight in a range of 175 kDa to 222 kDa.

* * * * *